United States Patent
Shibuya

(10) Patent No.: US 9,223,210 B2
(45) Date of Patent: Dec. 29, 2015

(54) PHOTOSENSITIVE COMPOUND, PHOTOSENSITIVE RESIN, AND PHOTOSENSITIVE COMPOSITION

(71) Applicant: TOYO GOSEI CO., LTD., Chiba (JP)

(72) Inventor: Toru Shibuya, Inzai (JP)

(73) Assignee: TOYO GOSEI CO., LTD., Chiba (JP)

( * ) Notice: Subject to any disclaimer, the term of this patent is extended or adjusted under 35 U.S.C. 154(b) by 0 days.

(21) Appl. No.: 14/391,170

(22) PCT Filed: Feb. 28, 2013

(86) PCT No.: PCT/JP2013/055423
§ 371 (c)(1),
(2) Date: Oct. 8, 2014

(87) PCT Pub. No.: WO2013/153873
PCT Pub. Date: Oct. 17, 2013

(65) Prior Publication Data
US 2015/0079519 A1 Mar. 19, 2015

(30) Foreign Application Priority Data

Apr. 9, 2012 (JP) ................................. 2012-088853

(51) Int. Cl.

| | |
|---|---|
| G03F 7/12 | (2006.01) |
| C08F 116/06 | (2006.01) |
| C07D 233/60 | (2006.01) |
| C07D 263/38 | (2006.01) |
| C07C 247/16 | (2006.01) |
| G03F 7/012 | (2006.01) |
| C07D 233/61 | (2006.01) |
| C07C 233/83 | (2006.01) |
| C07D 263/42 | (2006.01) |
| C07C 247/18 | (2006.01) |
| C07D 295/14 | (2006.01) |
| G03F 7/008 | (2006.01) |
| G03F 7/038 | (2006.01) |

(52) U.S. Cl.
CPC .............. *G03F 7/012* (2013.01); *C07C 233/83* (2013.01); *C07C 247/16* (2013.01); *C07C 247/18* (2013.01); *C07D 233/60* (2013.01); *C07D 233/61* (2013.01); *C07D 263/38* (2013.01); *C07D 263/42* (2013.01); *C07D 295/14* (2013.01); *C08F 116/06* (2013.01); *G03F 7/008* (2013.01); *G03F 7/0125* (2013.01); *G03F 7/0388* (2013.01)

(58) Field of Classification Search
None
See application file for complete search history.

(56) References Cited

U.S. PATENT DOCUMENTS

| | | | | |
|---|---|---|---|---|
| 3,617,170 | A * | 11/1971 | Hansen et al. | ...................... 8/638 |
| 4,728,594 | A * | 3/1988 | Nonogaki et al. | ............. 430/197 |
| 5,098,996 | A * | 3/1992 | Jacobson et al. | ............. 424/1.45 |
| 2004/0266901 | A1* | 12/2004 | Shibuya et al. | ..................... 522/1 |
| 2006/0222876 | A1* | 10/2006 | Kataoka et al. | ................ 428/500 |
| 2007/0072825 | A1 | 3/2007 | Williams | |
| 2009/0181158 | A1* | 7/2009 | Ikeya et al. | .................. 427/2.13 |

FOREIGN PATENT DOCUMENTS

| | | |
|---|---|---|
| JP | 2003-292477 | 10/2003 |
| JP | 2009-510083 | 3/2009 |
| WO | 2007/125894 | 11/2007 |

OTHER PUBLICATIONS

Cao, Yichen et al., Develpoment of Structure-Lipid Bilayer Permeability Relationships for Peptide-like Small Organic Molecules, Molecular Pharmaceutics, 2008, 5(3), p. 371-388.
International Search Report—PCT/JP2013/055423—May 28, 2013.

* cited by examiner

*Primary Examiner* — Cynthia Hamilton
(74) *Attorney, Agent, or Firm* — Young & Thompson

(57) ABSTRACT

A photosensitive compound represented by formula (1) or formula (2). (Chemical formula 1) (In formula (1) and formula (2), n is an integer of 1-3; $R^1$ is a linear or branched alkyl group having 1-6 carbon atoms or an alkylene group having 2-6 carbon atoms formed from two $R^1$ together; $R^2$ is $-NR^3R^4$; $R^3$ and $R^4$ are each independently a linear or branched alkyl group or alkenyl group having 1-6 carbon atoms, a linear or branched alkylene group having 2-6 carbon atoms formed by $R^3$ and $R^4$ together, or a linear or branched alkylene group or alkenylene group having 3-8 carbon atoms optionally containing an oxygen atom or nitrogen atom.)

11 Claims, 3 Drawing Sheets

PHOTOSENSITIVE COMPOUND, PHOTOSENSITIVE RESIN, AND PHOTOSENSITIVE COMPOSITION

TECHNICAL FIELD

An aspect of the present invention relates to a novel photosensitive compound, to a novel photosensitive resin, and to a novel photosensitive composition.

BACKGROUND ART

A variety of photosensitive compositions containing a photosensitive resin have been proposed for providing a resist used in a semiconductor lithography step or the like, a coating material for providing a substrate with a functional surface, or a similar material (see, for example, Patent Document 1). Such a photosensitive composition preferably contains, as a solvent, water instead of an organic solvent, from the viewpoint of an environmental problem. Therefore, the photosensitive resin is preferably synthesized not in an organic solvent or a water-organic solvent mixture, but in water containing no organic solvent. In the case where a substrate is coated with a photosensitive composition, to thereby provide a medical device, a biochemistry test device, or the like, elution, from a substrate, of a substance which adversely affects a living body or the like must be prevented. In such a case, use of a photosensitive composition containing, as a solvent, water instead of an organic solvent is particularly preferred.

The photosensitive resin may be produced through, for example, incorporating a photosensitive compound into a polymer. Patent Document 1 discloses a photosensitive compound which can be dissolved in water to a certain extent and which can be incorporated into a polymer through synthesis reaction in water. However, in order to produce, for example, a photosensitive resin from a higher concentration aqueous solution of a photosensitive compound, a photosensitive compound having a further high water solubility is desired.

Also preferably, the photosensitive composition has excellent storage stability and can be produced from an inexpensive material. However, the photosensitive composition disclosed in Patent Document 1 has problems in that the storage stability thereof is insufficient and that a photosensitive compound which can provide a synthetic photosensitive resin in water must be obtained from an expensive material.

PRIOR ART DOCUMENTS

Patent Documents

Patent Document 1: Japanese Patent Application Laid-Open (kokai) No. 2003-292477

SUMMARY OF THE INVENTION

Problems to be Solved by the Invention

In view of the foregoing, an object of an aspect of the present invention is to provide a photosensitive compound which has high water solubility, which can be produced from an inexpensive material, and which can produce a photosensitive composition having excellent storage stability. Another object is to provide a photosensitive resin produced from the photosensitive compound. Still another object is to provide a photosensitive composition containing the photosensitive resin.

Means for Solving the Problems

In one mode of an aspect of the present invention to solve the aforementioned problems, there is provided a photosensitive compound characterized by being represented by the following formula (1) or formula (2),

[Formula 1]

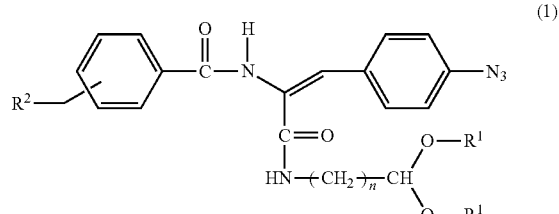

(1)

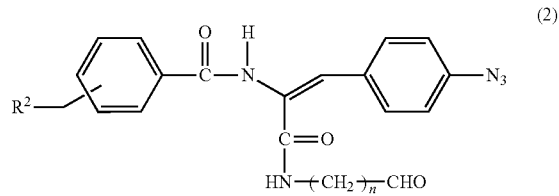

(2)

wherein: n is an integer of 1 to 3; $R^1$ represents a C1 to C6 linear or branched alkyl group, or a C2 to C6 alkylene group formed from two $R^1$ together; $R^2$ represents $-NR^3R^4$, where $R^3$ and $R^4$ each independently represent a C1 to C6 linear or branched alkyl group, or alkenyl group, or $R^3$ and $R^4$ together form a C2 to C6 linear or branched alkylene group, or form a C3 to C8 linear or branched alkylene group, or alkenylene group which may include an oxygen atom or a nitrogen atom.

Preferably, $R^1$ is a methyl group or an ethyl group, and $R^2$ is a group selected from the following groups,

[Formula 2]

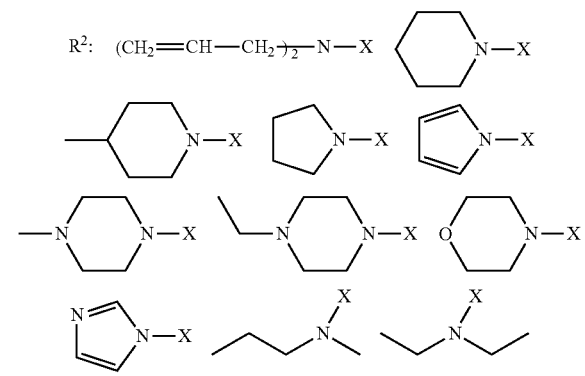

where X represents a substitution position.

In another mode of an aspect of the present invention, there is provided a photosensitive resin characterized by being formed by attaching the aforementioned photosensitive compound to a polyvinyl alcohol polymer having a structure in which at least two repeating units derived from vinyl alcohol are linked together, via an acetal bond in a pendant manner.

The photosensitive resin may contain a repeating unit represented by the following formula (3),

[Formula 3]

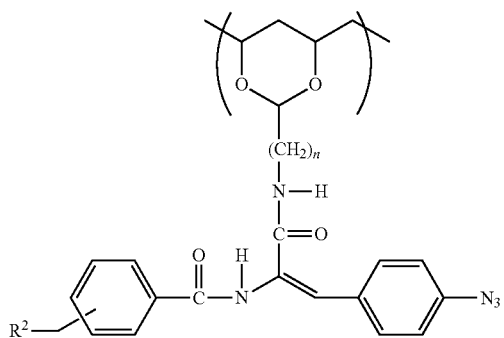

(3)

wherein n is an integer of 1 to 3, and $R^2$ represents a group selected from the following groups,

[Formula 4]

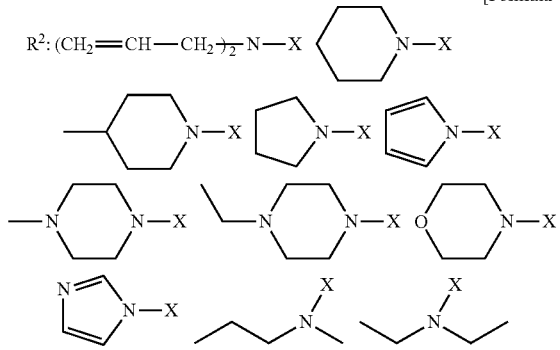

where X represents a substitution position.

The polyvinyl alcohol polymer may be a copolymer of a vinyl alcohol with at least one species selected from the group consisting of vinyl acetate, diacetoneacrylamide, acrylamide, acrylic acid, and polyethylene glycol.

In another mode of an aspect of the present invention, there is provided a photosensitive composition characterized by comprising the aforementioned photosensitive resin and water.

In another mode of an aspect of the present invention, there are provided compounds characterized by being represented by respectively the following formulas (4), (5), and (6):

[Formula 5]

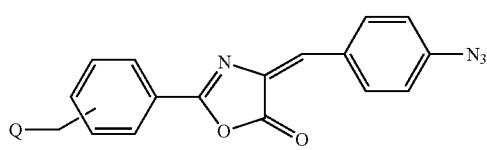

(4)

wherein Q represents a halogen atom;

[Formula 6]

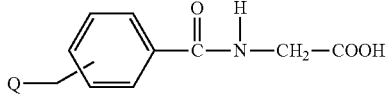

(5)

wherein Q represents a halogen atom;

[Formula 7]

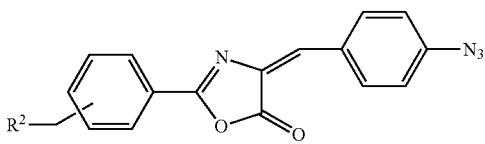

(6)

wherein $R^2$ represents —$NR^3R^4$, where $R^3$ and $R^4$ each independently represent a C1 to C6 linear or branched alkyl group, or alkenyl group, or $R^3$ and $R^4$ together form a C2 to C6 linear or branched alkylene group, or form a C3 to C8 linear or branched alkylene group, or alkenylene group which may include an oxygen atom or a nitrogen atom.

Effects of the Invention

According to an aspect of the present invention, there can be provided a photosensitive compound which can be produced from an inexpensive material and which has high water solubility. A photosensitive composition comprising: a photosensitive resin in which the photosensitive compound is incorporated into a polyvinyl alcohol polymer via an acetal bond in a pendant manner; and water, exhibits excellent storage stability for a long period of time.

MODES FOR CARRYING OUT THE INVENTION

Figure 1:
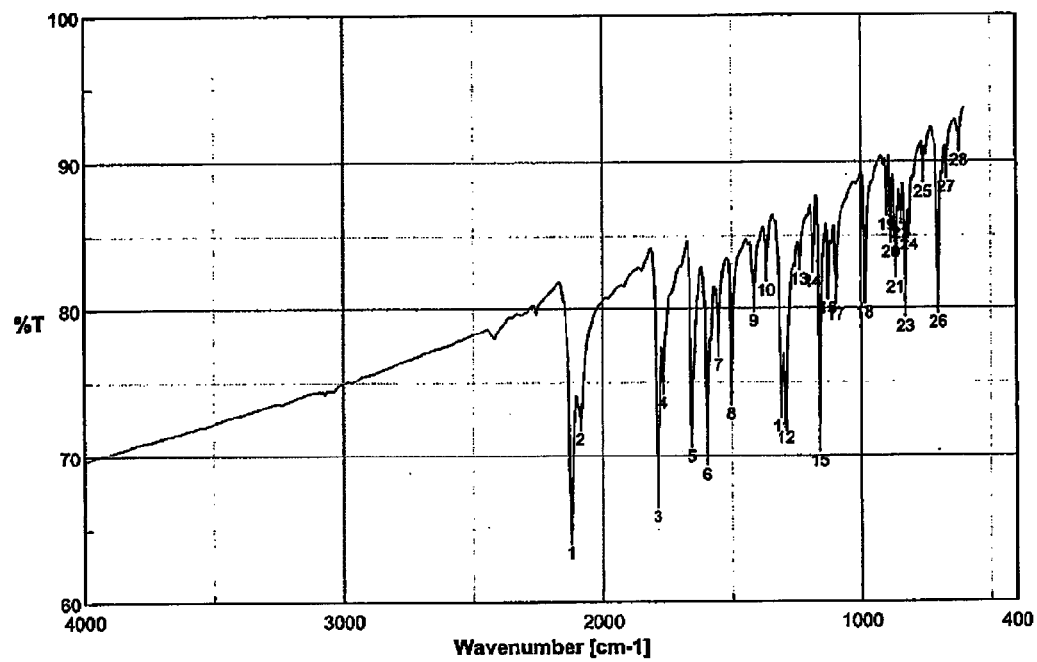
FIG. 1 An IR absorption spectrum of photosensitive material A produced in Example 1.

The photosensitive compound of an aspect of the present invention is an acetal compound or an aldehyde compound having a specific structure including an azido group and a tertiary amino group; i.e., a photosensitive compound represented by formula (1) or a photosensitive compound represented by formula (2). In formulas (1) and (2), $R^1$ represents a C1 to C6 linear or branched alkyl group, or a C2 to C6 alkylene group formed from two $R^1$ together; i.e., a C2 to C6 group —$R^1$—$R^1$—. From the viewpoint of cost, $R^1$ is preferably a methyl group or an ethyl group. $R^2$ represents —$NR^3R^4$ where $R^3$ and $R^4$ each independently represent a C1 to C6 linear or branched alkyl group, or alkenyl group, or $R^3$ and $R^4$ together form a C2 to C6 linear or branched alkylene group, or form a C3 to C8 linear or branched alkylene group, or alkenylene group which may include an oxygen atom or a nitrogen atom. From the viewpoint of cost, $R^2$ is preferably a group selected from among the following groups. In the following formulas, X represents a substitution position; i.e., a bonding position of the methylene group to a benzene ring. No particular limitation is imposed on the locant of $R^2$—$CH_2$— on the benzene ring, and $R^2$—$CH_2$— may be bonded to any of o-, m-, and p-positions with respect to —CONH— group bonded to the benzene ring. The number "n" is an integer of 1 to 3. From the viewpoint of favorable reactivity with a polyvinyl alcohol polymer, n is preferably 3.

[Formula 8]

$R^2$: $(CH_2$=$CH$—$CH_2)_{\overline{2}}$—$N$—$X$ (structures shown)

(wherein X represents a substitution position)

The photosensitive compounds of an aspect of the present invention represented by formulas (1) and (2) exhibit absorption wavelength in the range of 250 nm to 400 nm. That is, the photosensitive compounds have a photosensitive group which is sensitive to light having a wavelength of 400 nm or shorter.

The photosensitive compounds of an aspect of the present invention represented by formulas (1) and (2) exhibit considerably high solubility in an acidity range. For example, each of the compounds can be dissolved in an amount of ≥2 g (further ≥4 g) in 100 g of an acidic aqueous medium having a pH of 1.5 to 3. Also, the photosensitive compounds represented by formulas (1) and (2) are each an azide compound having an acetal group or an aldehyde group. Therefore, the photosensitive compounds represented by formulas (1) and (2) can undergo reaction in an acidic aqueous medium. Specifically, through reaction of a polymer having a structure in which two repeating units derived from vinyl alcohol are linked together, with the photosensitive compound in an acidic aqueous medium, the photosensitive compound can be bonded in a pendant manner to the polymer by the mediation of an acetal group or an aldehyde group. Thus, a target photosensitive resin can be synthesized without use of an organic solvent such as an alcohol, which problematically imposes an environmental load. In addition, since the photosensitive resin can be synthesized in water as a reaction solvent, removal of an organic solvent is not needed after synthesis of the photosensitive resin. The reaction mixture itself, or its water-diluted product may serve as a target aqueous photosensitive composition containing no organic solvent. Meanwhile, the photosensitive compound represented by formula (1) or (2) exhibits considerably high solubility in an acidity range, and a high-concentration aqueous solution of the compound undergoes acetalization with a polymer, to thereby yield the polymer to which the photosensitive compound is bonded in a pendant manner. The thus-produced photosensitive composition exhibits no rise in viscosity even after storage for a long period of time, to thereby attain excellent storage stability. Although details will be described hereinbelow, the photosensitive compounds represented by formulas (1) and (2) can be prepared from inexpensive raw materials.

In contrast, conventional photosensitive compounds generally have poor water solubility. Such a compound encounters difficulty in pendant-manner bonding the compound to a polymer in water as a single reaction solvent. Patent Document 1 discloses a photosensitive compound having water solubility, and the photosensitive compound can be reacted with a polymer in water, to thereby bond the photosensitive compound to the polymer in a pendant manner. However, the water-soluble photosensitive compounds disclosed in Patent Document 1 would have water solubility slightly lower than that of the photosensitive compound of an aspect of the present invention represented by formula (1) or (2). Thus, a photosensitive composition containing a photosensitive resin formed of a polymer to which the photosensitive compound has been bonded in a pendant manner in water has poor long-term storage stability. Among the photosensitive compounds disclosed in Patent Document 1, the photosensitive compound of Synthesis Example 5 exhibits relatively high water solubility. However, the water solubility is lower than that of the photosensitive compound of an aspect of the present invention, as described in the below-mentioned Comparative Synthesis Example 2. The photosensitive composition prepared from such a conventional photosensitive compound exhibits poor long-term storage stability. Also, photosensitive compounds disclosed in Synthesis Example 5 and other Synthesis Examples of Patent Document 1 each have a pyridine structure, which conceivably imparts water solubility to the compounds. However, in order to incorporate a pyridine structure, an expensive raw material such as pyridinealdehyde must be used, which is problematic.

No particular limitation is imposed on the method for synthesizing the photosensitive compounds represented by formulas (1) and (2). For example, as illustrated in the following reaction scheme, the photosensitive compound represented by formula (1) can be produced by reacting a compound represented by formula (a) having a halomethyl group with a secondary amine compound $NR^3R^4H$. In formula (a), n and $R^1$ have the same meanings as employed in formula (1), and Q represents a halogen atom, for example, a chlorine atom or a bromine atom. The reaction may be performed in a solvent such as acetonitrile for about 3 to about 8 hours in the presence of triethylamine or the like.

[Formula 9]

(structure shown)

(a)

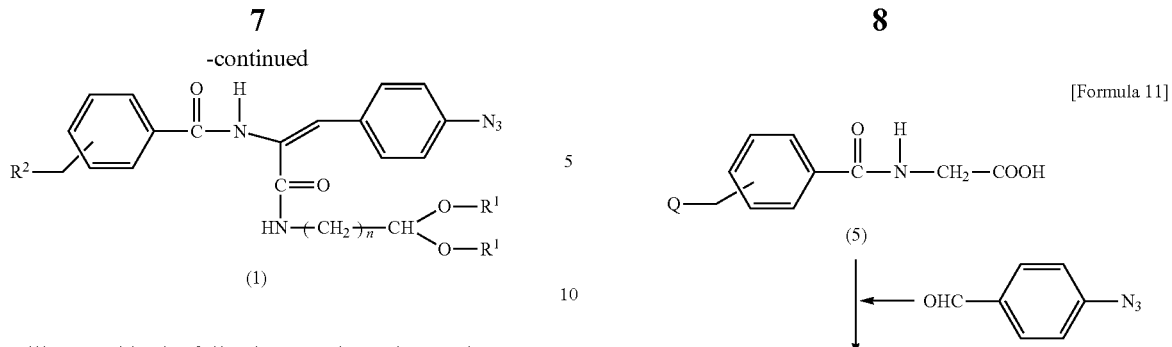

As illustrated in the following reaction scheme, the compound represented by formula (a) having a halomethyl group may be produced by reacting a compound represented by formula (4) having an azlactone ring with an acetal compound represented by formula (b). In formula (b), n and $R^1$ have the same meanings as employed in formula (1), and Q is the same as employed in formula (a). The reaction may be performed in a solvent such as tetrahydrofuran for about 3 to about 8 hours in the absence of a catalyst.

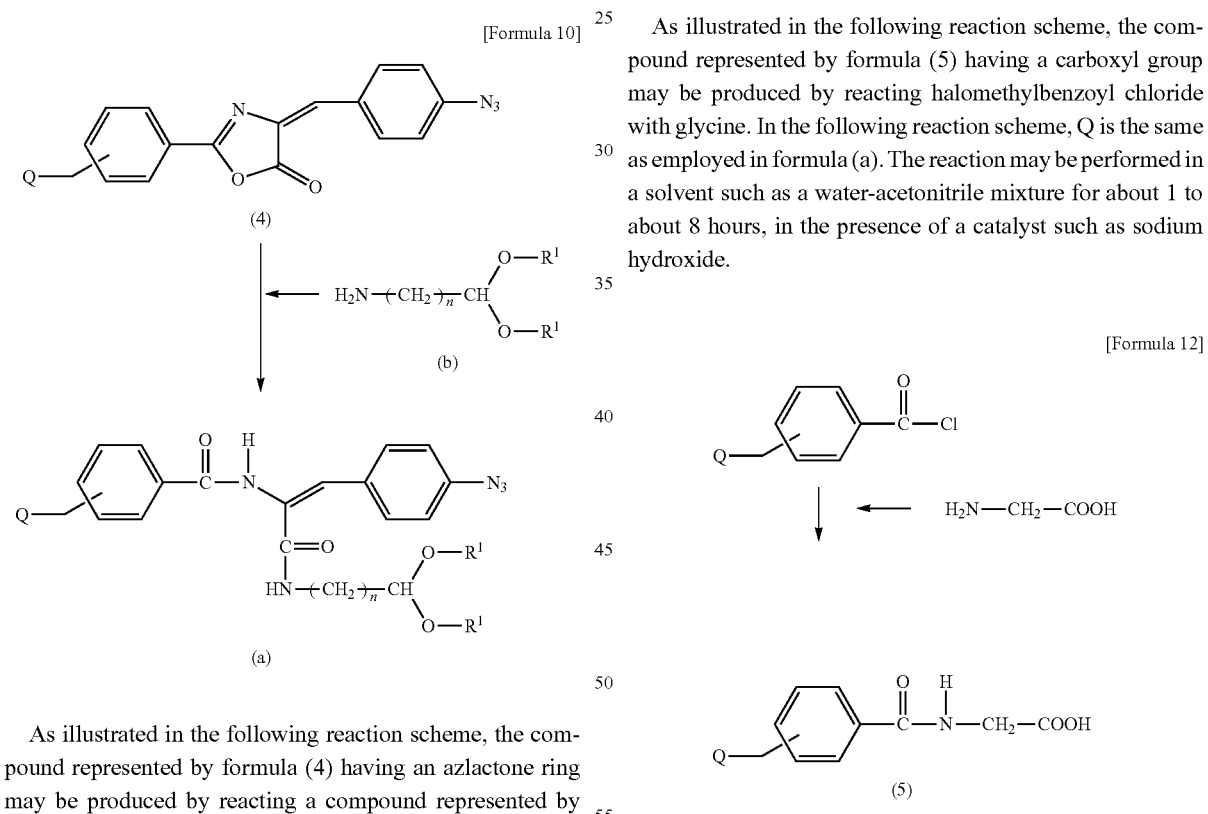

As illustrated in the following reaction scheme, the compound represented by formula (4) having an azlactone ring may be produced by reacting a compound represented by formula (5) having a carboxyl group with azidobenzaldehyde. In formula (5), Q is the same as employed in formula (a). The reaction may be performed in a solvent such as acetonitrile for about 5 to about 12 hours in the presence of acetic anhydride, sodium acetate, and the like. Alternatively, the compound represented by formula (4) may be produced by adding ethyl chloroformate to a compound represented by formula (5) in a solvent such as acetonitrile in the presence of a base such as triethylamine, to thereby form an azlactone ring, and further reacting with azidobenzaldehyde.

As illustrated in the following reaction scheme, the compound represented by formula (5) having a carboxyl group may be produced by reacting halomethylbenzoyl chloride with glycine. In the following reaction scheme, Q is the same as employed in formula (a). The reaction may be performed in a solvent such as a water-acetonitrile mixture for about 1 to about 8 hours, in the presence of a catalyst such as sodium hydroxide.

As illustrated in the following reaction scheme, the photosensitive compound represented by formula (1) may be produced by reacting a compound represented by formula (6) with the acetal compound represented by formula (b). In formula (6), $R^2$ has the same meaning as employed in formula (1). In formula (b), n and $R^1$ have the same meanings as employed in formula (1). The reaction may be performed in a solvent such as tetrahydrofuran for about 1 to about 5 hours in the absence of a catalyst.

[Formula 13]

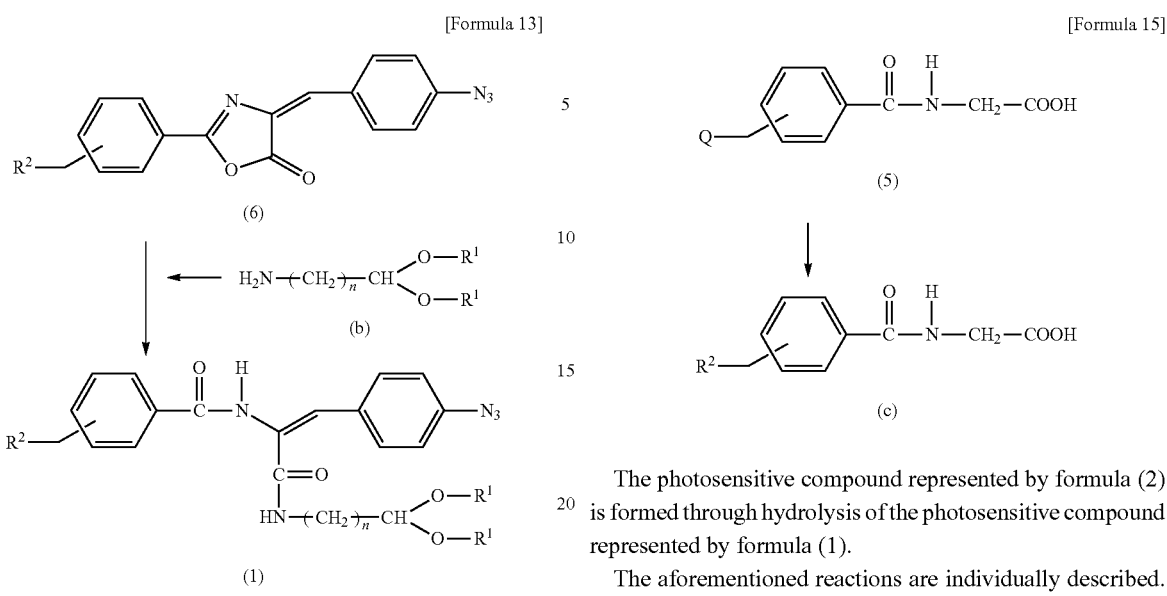

As illustrated in the following reaction scheme, the photosensitive compound represented by formula (6) may be produced by reacting a compound represented by formula (c) having a carboxyl group with azidobenzaldehyde. In formula (c), $R^2$ has the same meaning as employed formula (1). The reaction may be performed in a solvent such as acetonitrile for about 5 to about 12 hours in the presence of acetic anhydride or the like. Alternatively, the photosensitive compound represented by formula (6) may be produced by adding ethyl chloroformate to the compound represented by formula (c) having a carboxyl group in a solvent such as acetonitrile in the presence of a base such as triethylamine, to thereby form an azlactone ring, and further reacting with azidobenzaldehyde.

[Formula 14]

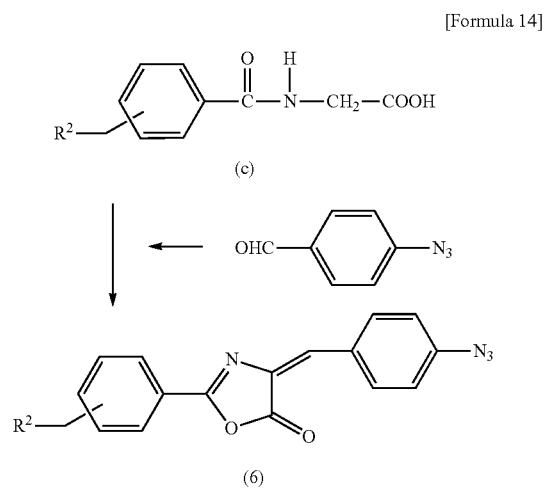

As illustrated in the following reaction scheme, the compound represented by formula (c) can be produced by reacting the compound represented by formula (5) having a carboxyl group with a secondary amine compound $NR^3R^4H$. In formula (5), Q represents a halogen atom. In formula (c), $R^2$ has the same meaning as employed in formula (1). The reaction may be performed in a solvent such as water or acetonitrile for about 3 to about 12 hours in the presence of triethylamine or the like.

[Formula 15]

The photosensitive compound represented by formula (2) is formed through hydrolysis of the photosensitive compound represented by formula (1).

The aforementioned reactions are individually described. However, needless to say, these reactions may be in sequential steps. The aforementioned compounds represented by formulas (4) to (6) and those represented by formulas (a) and (c) are novel compounds.

Through bonding of the photosensitive compound represented by formula (1) or (2) to, via an acetal bond in a pendant manner, a polyvinyl alcohol polymer having a structure in which at least two repeating units derived from vinyl alcohol are linked together, the photosensitive resin of an aspect of the present invention is yielded.

The photosensitive resin of an aspect of the present invention, having, in a side chain thereof, a structure originating from the aforementioned photosensitive compound represented by formula (1) or (2), exhibits photo-crosslinkability. Specifically, through irradiation with light having a wavelength in the range of 250 nm to 400 nm, the photosensitive resin undergoes crosslinking, to thereby form a photocured body. The photosensitive resin of an aspect of the present invention exhibits photo-crosslinkability, when a photosensitive compound represented by formula (1) or (2) has been bonded to the polyvinyl alcohol polymer skeleton via an acetal bond in a pendant manner. For example, a photosensitive compound represented by formula (1) or (2) is preferably bonded to the polyvinyl alcohol polymer skeleton in an amount of 0.1 mol % to 3 mol % via an acetal bond in a pendant manner. In the case where a plurality of photosensitive compounds represented by formula(s) (1) and/or (2) is or are bonded to the polyvinyl alcohol polymer skeleton via an acetal bond in a pendant manner, the total amount of the photosensitive compounds represented by formulas (1) and (2) are preferably bonded in an amount of 0.1 mol % to 3 mol % via an acetal bond in a pendant manner, to a structure in which at least two repeating units derived from vinyl alcohol are linked together.

Notably, the repeating unit derived from vinyl alcohol is a structure formed from vinyl alcohol as a monomer and has the following chemical structure.

[Formula 16]

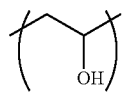

The structure in which at least two repeating units derived from vinyl alcohol are linked together refers to the following structure.

[Formula 17]

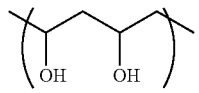

The polyvinyl alcohol polymer may be polyvinyl alcohol or a copolymer of vinyl alcohol and another vinyl compound. Examples of the copolymer include copolymers of vinyl alcohol and at least one member selected from the group consisting of vinyl acetate, diacetoneacrylamide, acrylamide, acrylic acid, and polyethylene glycol. The mode of the copolymer may be random, block, or graft. In the copolymer, the repeating unit derived from vinyl alcohol is preferably included in an amount of 70 weight % or more.

In an aspect of the present invention, polyvinyl alcohol preferably has an average polymerization degree of, for example, 200 to 5,000. When the average polymerization degree is less than 200, sufficient photosensitivity fails to be attained, whereas when the average polymerization degree is in excess of 5,000, the formed photosensitive resin has high viscosity, readily impairing applicability, which is disadvantageous. If the concentration is reduced to lower the viscosity, difficulty is encountered in ensuring a target coating thickness. Examples of the copolymer of vinyl alcohol and another vinyl compound include a vinyl copolymer having an average polymerization degree of 200 to 5,000.

Through acetalization of the polyvinyl alcohol polymer with the photosensitive compound represented by formula (1) or (2) in water as a reaction solvent under acidic conditions, the photosensitive resin of an aspect of the present invention can be yielded. No particular limitation is imposed on the reaction conditions, and acetalization is preferably performed in an aqueous medium having a pH in the range of 1.5 to 3, adjusted by the addition of phosphoric acid, p-toluenesulfonic acid, or the like. The acetalization reaction may be performed at about 50° C. to about 70° C. for about 5 to about 48 hours. Meanwhile, there may be also added to the acetalization reaction an aliphatic aldehyde such as formaldehyde, acetaldehyde, propionaldehyde, butyladehyde, or crotonaldehyde; an aromatic aldehyde such as benzaldehyde, benzaldehyde sulfonate salt, benzaldehyde dislufonate salt, sodium 4-azido-2-sulfobenzaldehyde, carboxybenzaldehyde, hydroxybenzaldehyde, or a folmylstyrylpyrudinium salt; an acetal thereof; or a ketone such as acetone or methyl ethyl ketone.

The photosensitive composition of an aspect of the present invention contains the aforementioned the photosensitive resin of an aspect of the present invention and water. No particular limitation is imposed on the photosensitive resin content of the photosensitive composition of an aspect of the present invention. For example, the photosensitive composition may have a photosensitive resin concentration of 4 to 15 weight %.

The photosensitive composition of an aspect of the present invention may further contain, in addition to the photosensitive resin of an aspect of the present invention, a water-soluble polymer and/or a water-soluble azide compound.

Examples of the water-soluble polymer include saponified polyvinyl acetate, natural polymers (e.g., gelatin, cellulose derivatives, and casein), and a homopolymer or a copolymer of a water-soluble vinyl monomer. Examples of the water-soluble vinyl monomer include N-vinylformamide, N-vinylacetamide, vinylpyrrolidone, acrylamide, diacetoneacrylamide, N,N-dimethylacrylamide, vinylpyridine, methacrylamide, allylthiourea and the like.

Examples of the water-soluble azide compound include 4,4'-diazidostilbene-2,2'-disulfonic acid, 4,4'-diazidobenzalacetophenone-2-sulfonic acid, 4,4'-diazidostilbene-α-carboxylic acid, and an alkali metal salt, an ammonium salt, an organic amine salt, or the like thereof. Furthermore, preferably used are water-soluble azide compounds disclosed in Japanese Patent Publication (kokoku) No. Sho 50-27404, Japanese Patent Application Laid-Open (kokai) Nos. Sho 50-141403, Hei 2-204750, Hei 4-26849, Hei 5-11442, Hei 5-113661, Hei 6-239930, and other documents.

For improving coating applicability and moisture-keeping property, the photosensitive composition of an aspect of the present invention may further contain, for example, ethylene glycol, sorbitol, a surfactant or the like.

Also, the photosensitive composition of an aspect of the present invention may further contain a so-called silane coupling agent, which is an adhesion promoter for improving adhesion to a substrate. Examples of the adhesion promoter include water-soluble adhesion promoters such as N-β-(aminoethyl)-aminopropylmethyldimethoxysilane and N-β-(aminoethyl)-γ-aminopropyltrimethoxysilane.

The photosensitive composition of an aspect of the present invention may further contain an antiseptic agent, a defoaming agent, or a pH-modifying agent, or a hydrophobic polymer emulsion for improving film strength, water resistance, adhesion to various substrates, and other purposes. Examples of the hydrophobic emulsion include polyvinyl acetate emulsion, polyacrylate ester emulsion, and urethane emulsion. A pattern formation technique employing a composition containing a hydrophobic polymer emulsion is suitably used in, for example, production of a screen printing plate.

For preventing halation upon exposure and obtaining a colored image, the photosensitive composition of an aspect of the present invention may further contain a colorant such as a pigment or a dye.

As illustrated in the below-mentioned Examples, the photosensitive composition of an aspect of the present invention has resistance to viscosity rise even after long-term storage, indicating excellent storage stability.

As described above, the photosensitive resin of an aspect of the present invention can be synthesized by use of water as a reaction solvent, instead of an organic solvent. Therefore, the as-synthesized photosensitive resin itself can be used without removal of organic solvent. Alternatively, the photosensitive resin may be optionally diluted with water or the like, to thereby provide an aqueous photosensitive composition free from organic solvent. Needless to say, in a yet alternative manner, a photosensitive resin is recovered from the reaction mixture, and water is added to the recovered resin.

The thus-prepared organic solvent-free photosensitive composition is suitably applied onto a substrate, to thereby produce a medical device, a biochemical test device, or the like. More specifically, when a photosensitive composition containing an organic solvent is applied onto a substrate made of a plastic material or the like, a substance (e.g., a plasticizer)

is readily eluted from the substrate, the substance adversely affecting bio materials such as protein, cells, enzymes, etc. Therefore, difficulty is encountered in employing, as a medical device or a biochemical test device, a substrate coated with such a photosensitive composition containing an organic solvent. In contrast, an aspect of the present invention provides a photosensitive composition which contains water as a solvent, instead of an organic solvent. Therefore, even when a substrate made of a plastic material or the like is coated with the composition of an aspect of the present invention, problematic elution which would otherwise be caused by organic solvent can be prevented, whereby the coated substrate can be employed as a medical device, a biochemical test device, or the like which is to be brought into contact with a biomaterial such as protein, cells, or enzymes.

No particular limitation is imposed on the material of the substrate, and examples thereof include glass and plastic material. Also, no particular limitation is imposed on the form of the substrate, and examples thereof include fiber, film, plate, and a substrate with pores.

Through applying the photosensitive composition of an aspect of the present invention onto the aforementioned substrate, optionally drying, and then irradiating the formed coating with light having a wavelength in the range of, for example, 250 nm to 400 nm, a photocured layer in which the photosensitive resin has been cross-linked can be formed on the substrate. When light irradiation is performed by the mediation of a mask having a specific pattern, a photocured layer having a specific pattern can be formed on the substrate, after washing with water. The thus-produced substrate on which a photocured layer has been formed can be employed as a medical device or a biochemical test device, such as a biochip, a biosensor, a cell culture container, a protein analysis container, an enzymatic reactor, or a flow-path protein analysis container. Such a substrate may also be employed for immobilization of a biocatalyst such as an enzyme or a microorganism. By virtue of high resolution, the photosensitive composition of an aspect of the present invention can be employed not only in production of the aforementioned medical devices and biochemical test devices and for immobilization of a biocatalyst, but also as a resist for use in, for example, a lithography step of forming a semiconductor micropattern.

EXAMPLES

An aspect of the present invention will next be described in detail by way of examples, which should not be construed as limiting the invention thereto.

Synthesis Example 1

Synthesis of Chloromethylbenzoylglycine Represented by the Following Formula

[Formula 18]

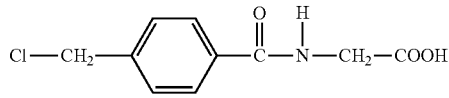

Glycine (3 g) was dissolved in a mixture of water (20 g), acetonitrile (10 g), and sodium hydroxide (2 g), and the solution was cooled to 10° C., to thereby prepare a glycine solution. Separately, chloromethylbenzoyl chloride (8 g) was dissolved in acetonitrile (20 g), and the solution was cooled to 10° C. The liquid was added dropwise to the glycine solution over 2 hours. Simultaneously a solution of sodium hydroxide (2 g) in water (20 g) was added dropwise to the glycine solution over 2 hours. Five hours later, the solution was acidified with 5 weight % aqueous hydrochloric acid, to thereby precipitate chloromethylbenzoylglycine as a target product. The precipitated product was separated through filtration and dried, to thereby yield 7 g of chloromethylbenzoylglycine as a target product.

Example 1

Synthesis of (4-(4-azidophenylmethylene)-2-(4-chloromethylphenyl)-1,3-oxazolin-5-one) represented by the following formula [photosensitive material A]

[Formula 19]

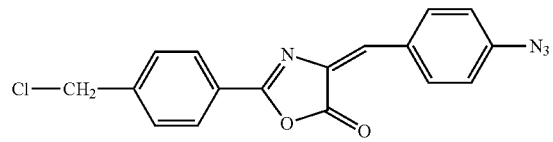

To chloromethylbenzoylglycine (7 g) produced in Synthesis Example 1, acetonitrile (2 g), azidobenzaldehyde (5 g), acetic anhydride (15 g), and sodium acetate (0.3 g) were added, and the mixture was allowed to react at 75° C. for 10 hours. The reaction mixture was cooled and subjected to filtration and drying, to thereby yield 6 g of photosensitive material A as a target compound. An IR absorption spectrum of photosensitive material A was measured through KBr method, and an absorption peak attributed to an azido group was identified at 2123.2 cm$^{-1}$. Also, an absorption peak attributed to azlactone was identified at 1787.7 cm$^{-1}$. FIG. 1 illustrates the IR absorption spectrum of photosensitive material A.

Synthesis Example 2

Synthesis of (3-(4-azidophenyl)-N-(4,4'-dimethoxybutyl)-2-(4-chloromethylphenyl)carbonylaminoprop-2-enamide) represented by the following formula [photosensitive material B]

[Formula 20]

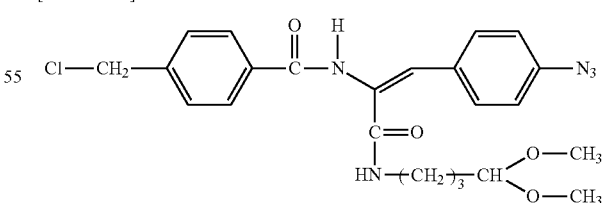

Photosensitive material A (6 g) produced in Example 1 was dispersed in tetrahydrofuran (hereinafter abbreviated as THF) (30 g). A solution of aminobutylaldehyde dimethylacetal (3 g) dissolved in THF (20 g) was added dropwise to the dispersion over 1 hour, while the mixture was cooled to maintain at 10° C. Thereafter, the mixture was allowed to stand for 3 hours, and water (150 g) was added thereto. The formed precipitates were separated through filtration and dried, to thereby yield 6 g of photosensitive material B as a target compound.

Example 2

Synthesis of (3-(4-azidophenyl)-N-(4,4'-dimethoxy-butyl)-2-(4-morpholinomethylphenyl)carbonylamino-prop-2-enamide) represented by the following formula [photosensitive material C]

[Formula 21]

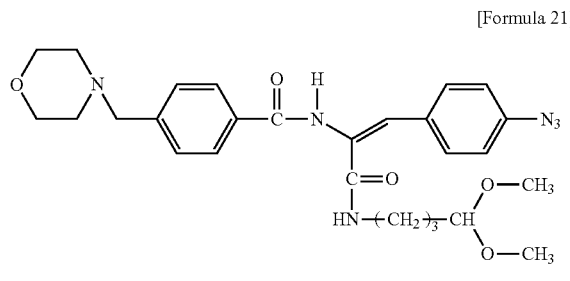

Figure 2:
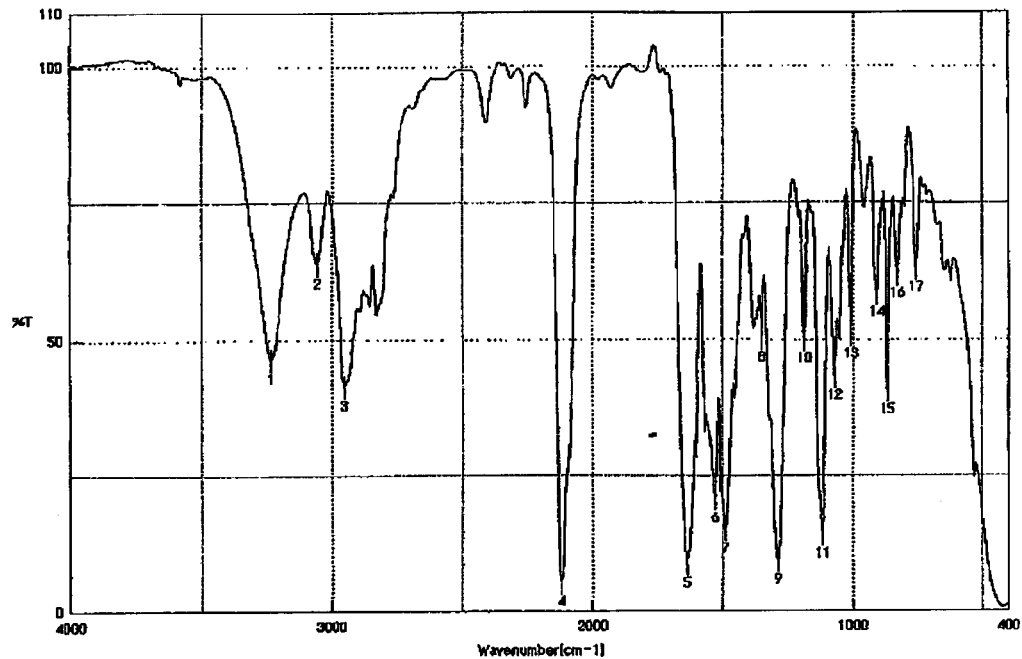
FIG. 2 An IR absorption spectrum of photosensitive material C produced in Example 2.

The compound produced in Synthesis Example 2 [photosensitive material B] (6 g), morpholine (1.3 g), and triethylamine (1.1 g) were dissolved in acetonitrile (40 g), and the solution was allowed to react at 50° C. for 7 hours later cooling, water (250 g) was added to the reaction mixture, and the formed precipitates were separated through filtration and dried, to thereby yield 4 g of photosensitive material C as a target compound. An IR absorption spectrum of photosensitive material C was measured through KBr method, and an absorption peak attributed to an azido group was identified at 2019.4 $cm^{-1}$. FIG. 2 illustrates the IR absorption spectrum of photosensitive material C.

Example 3

Synthesis of (3-(4-azidophenyl)-N-(4,4'-dimethoxy-butyl)-2-(4-imidazolylmethylphenyl)carbonylamino-prop-2-enamide) represented by the following formula [photosensitive material D]

[Formula 22]

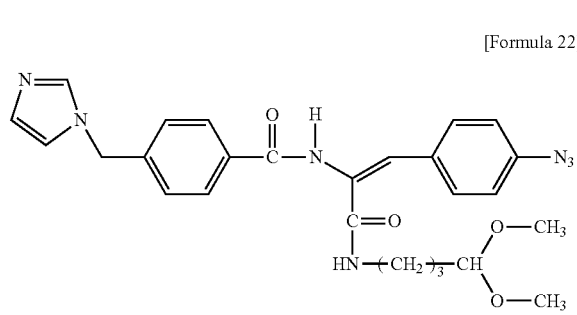

The compound produced in Synthesis Example 2 [photosensitive material B] (6 g), imidazole (1.3 g), and triethylamine (1.1 g) were dissolved in acetonitrile (40 g), and the solution was allowed to react at 50° C. for 7 hours later cooling, water (250 g) was added to the reaction mixture, and the formed precipitates were separated through filtration and dried, to thereby yield 2 g of photosensitive material D as a target compound.

Example 4

Synthesis of (3-(4-azidophenyl)-N-(4,4'-dimethoxy-butyl)-2-(4-diallylaminomethylphenyl)carbonylamino-prop-2-enamide) represented by the following formula [photosensitive material E]

[Formula 23]

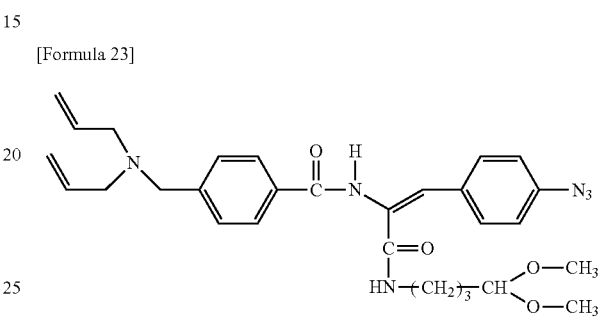

The compound produced in Synthesis Example 2 [photosensitive material B] (6 g), diallylamine (1.3 g), and triethylamine (1.1 g) were dissolved in acetonitrile (40 g), and the solution was allowed to react at 50° C. for 7 hours later cooling, water (250 g) was added to the reaction mixture, and the formed precipitates were separated through filtration and dried, to thereby yield 3 g of photosensitive material E as a target compound.

Example 5

Synthesis of (3-(4-azidophenyl)-N-(3-formylpropyl)-2-(4-morpholinomethylphenyl)carbonylamino-prop-2-enamide) represented by the following formula [photosensitive material F]

[Formula 24]

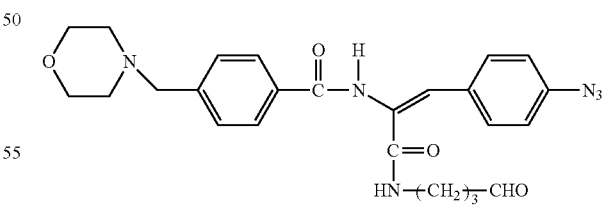

The compound produced in Example 2 [photosensitive material C] (2 g) was added to a mixture of water (40 g) and phosphoric acid (0.5 g), and the resultant mixture was stirred at 20° C. for 5 hours, to thereby remove the acetal protective group. Thereafter, the temperature of the deprotected mixture was adjusted to 10° C. and neutralized with 1 weight % aqueous sodium hydroxide to a pH of 8. The precipitates formed through neutralization were immediately separated through filtration and dried, to thereby yield 1 g of photosensitive material F as a target compound.

Example 6

Synthesis of (4-(4-azidophenylmethylene)-2-(4-morpholinomethylphenyl)-1,3-oxazolin-5-one) represented by the following formula [photosensitive material G]

[Formula 25]

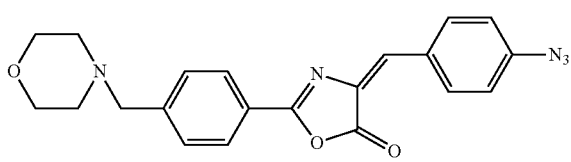

Figure 3:
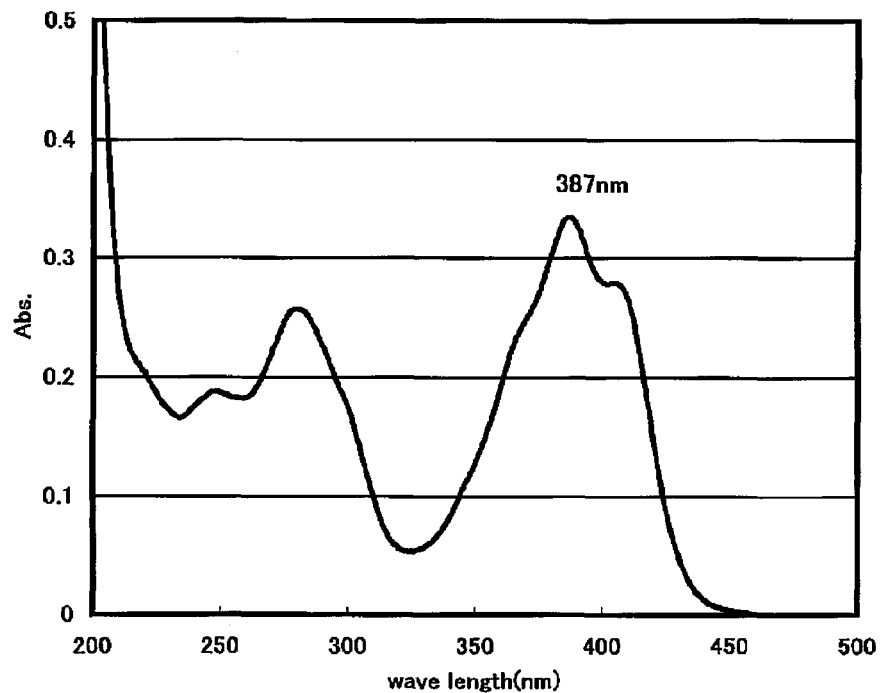
FIG. 3 A UV absorption spectrum of photosensitive material G produced in Example 6.

Glycine (3 g) was dissolved in a mixture of water (20 g), acetonitrile (10 g), and sodium hydroxide (2 g), and the solution was cooled to 10° C., to thereby prepare a glycine solution. Separately, chloromethylbenzoyl chloride (8 g) was dissolved in acetonitrile (20 g), and the solution was cooled to 10° C. The liquid was added dropwise to the glycine solution over 2 hours. Simultaneously, a solution of sodium hydroxide (2 g) dissolved in water (20 g) was added to the glycine solution over 2 hours. Five hours later, morpholine (4 g) was added thereto, and the mixture was allowed to react at 60° C. for 4 hours, followed by cooling the resultant solution to 10° C. Triethylamine (4 g) was further added, and then ethyl chloroformate (4.5 g) was added dropwise thereto over 30 minutes. The resultant mixture was continuously stirred for 2 hours. Subsequently, azidobenzaldehyde (3.5 g) was added, and the mixture was allowed to react at 20° C. for 16 hours. The thus-formed precipitates were separated through filtration and dried, to thereby yield 1 g of photosensitive material G as a target compound. Photosensitive material G was dissolved in acetonitrile, and a UV absorption spectrum of the solution was measured, and an absorption peak attributed to an azlactone ring was identified at 387 nm. FIG. 3 illustrates the UV absorption spectrum of photosensitive material G.

Example 7

Synthesis of (4-(4-azidophenylmethylene)-2-(4-morpholinomethylphenyl)-1,3-oxazolin-5-one) [photosensitive material G] (synthetic route different from that of Example 6)

Chloromethylbenzoylglycine (10 g) produced in Synthesis Example 1 was dispersed in acetonitrile (30 g), and triethylamine (4.5 g) and morpholine (4 g) were added to the dispersion. The mixture was allowed to react at 60° C. for 4 hours, to thereby form morpholinomethylbenzoylglycine. The reaction mixture was cooled to 10° C. Triethylamine (4.5 g) was further added, and then ethyl chloroformate (5 g) was added dropwise thereto over 30 minutes. The resultant mixture was continuously stirred for 2 hours. Subsequently, azidobenzaldehyde (6 g) was added, and the mixture was allowed to react at 20° C. for 16 hours. The thus-formed precipitates were separated through filtration and dried, to thereby yield 6 g of photosensitive material G as a target compound. Photosensitive material G was dissolved in acetonitrile, and a UV absorption spectrum of the solution was measured, and an absorption peak attributed to an azlactone ring was identified at 387 nm. An IR absorption spectrum of photosensitive material G was measured through KBr method, and an absorption peak attributed to an azido group was identified at 2115.5 cm$^{-1}$. Also, an absorption peak attributed to azlactone was identified at 1792.5 cm$^{-1}$.

Example 8

Synthesis of (3-(4-azidophenyl)-N-(4,4'-dimethoxybutyl)-2-(4-morpholinomethylphenyl)carbonylamino-prop-2-enamide) [photosensitive material C] (synthetic route different from that of Example 2)

Photosensitive material G (6 g) produced in Example 7 was dispersed in THF (30 g). A solution of aminobutylaldehyde dimethylacetal (3 g) dissolved in THF (20 g) was added dropwise to the dispersion over 1 hour, while the mixture was cooled to maintain at 10° C. Thereafter, the mixture was allowed to stand for 3 hours, and water (150 g) was added thereto. The formed precipitates were separated through filtration and dried, to thereby yield 5 g of photosensitive material C as a target compound. An IR absorption spectrum of photosensitive material C was measured through KBr method, and an absorption peak attributed to an azido group was identified at 2019.4 cm$^{-1}$.

Comparative Synthesis Example 1

Synthesis of (3-(4-azidophenyl)-N-(4,4'-dimethoxybutyl)-2-phenylcarbonylamino-prop-2-enamide) represented by the following formula [comparative photosensitive material H]

[Formula 26]

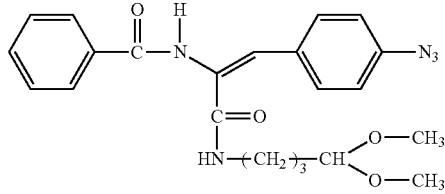

Comparative photosensitive material H represented by the above formula was yielded in accordance with Synthesis Example 1 disclosed in Japanese Patent Application Laid-Open (kokai) No 2003-292477.

Comparative Synthesis Example 2

Synthesis of (2-(3-(4-azidophenyl)prop-2-enoylamino)-N-(4,4-dimethoxybutyl)-3-(3-pyridyl)prop-2-enamide) represented by the following formula [comparative photosensitive material I]

[Formula 27]

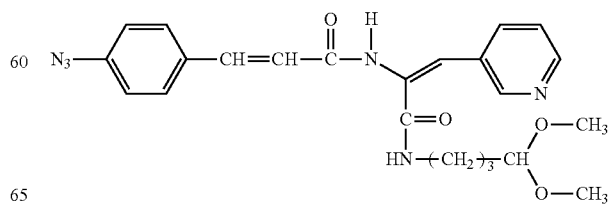

Comparative photosensitive material I represented by the above formula was yielded in accordance with Synthesis Example 5 disclosed in Japanese Patent Application Laid-Open (kokai) No 2003-292477.

Example 9

Synthesis of Photosensitive Resin J and Preparation of a Photosensitive Composition Polyvinyl alcohol (Gohsenol EG-30, product of The Nippon Synthetic Chemical Industry Co., Ltd., average polymerization degree: 1,700) (40 g) was dissolved in water (400 g), and photosensitive material C (4 g) produced in Example 2 and phosphoric acid (2 g) were added to the solution. The mixture was allowed to react at 60° C. for 24 hours. Percent acetalization, determined through GPC (gel permeation chromatography), was 98%. The acetalization amount, calculated from the percent acetalization, was 0.8 mol % based on polyvinyl alcohol. Thereafter, phosphoric acid was removed through treatment with an ion exchange resin, to thereby yield a photosensitive liquid containing a photosensitive resin in which photosensitive material C is bonded to polyvinyl alcohol via an acetal bond in a pendant manner. The photosensitive liquid was diluted with water, to thereby prepare a photosensitive composition having a photosensitive resin concentration of 6 weight %.

The thus-prepared photosensitive composition was applied onto a glass plate and dried, to thereby form a coating film having a film thickness of 1.0 μm. A test mask (product of TOPPAN Printing Co., Ltd.) was firmly attached to the coating film, and the film was irradiated via the mask with light of an ultrahigh-pressure mercury lamp (UV illuminance: 5 mW/cm$^2$, determined by means of an illuminometer "UV-35," product of ORC Manufacturing Co., Ltd.) for 15 seconds. Subsequently, the light-exposed film was developed with water over 60 seconds and dried. Thus, a clear pattern having a line width of 30 μm and no development residue was obtained through the development step.

Figure 4:
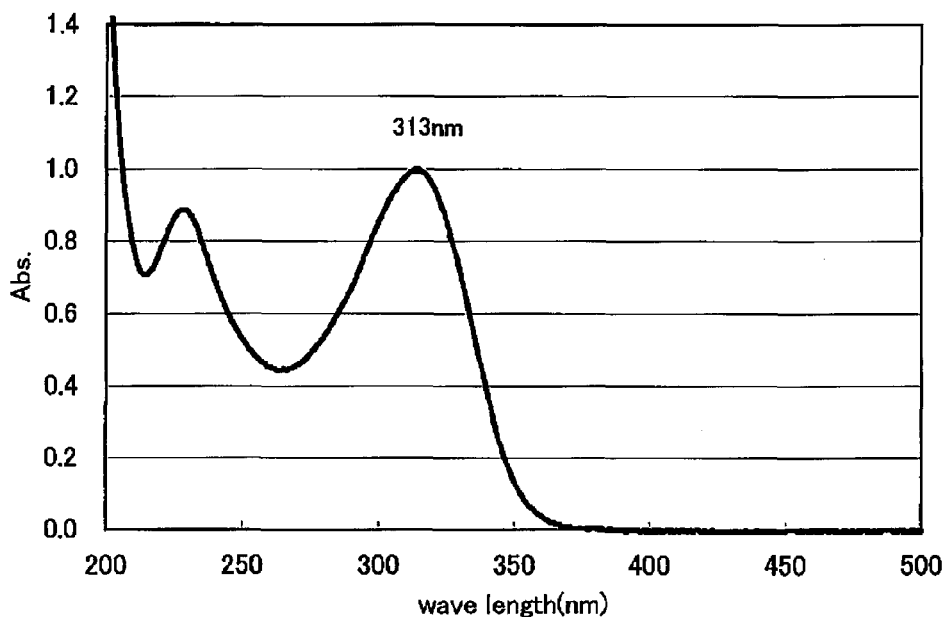
FIG. 4 A UV absorption spectrum of coating film of photosensitive resin J produced in Example 9.

Separately, a UV absorption spectrum of the coating film formed by applying the prepared photosensitive composition onto a glass plate and drying was measured. The spectrum was found to have an absorption peak at 313.6 nm. FIG. 4 illustrates the UV absorption spectrum.

Figure 5:
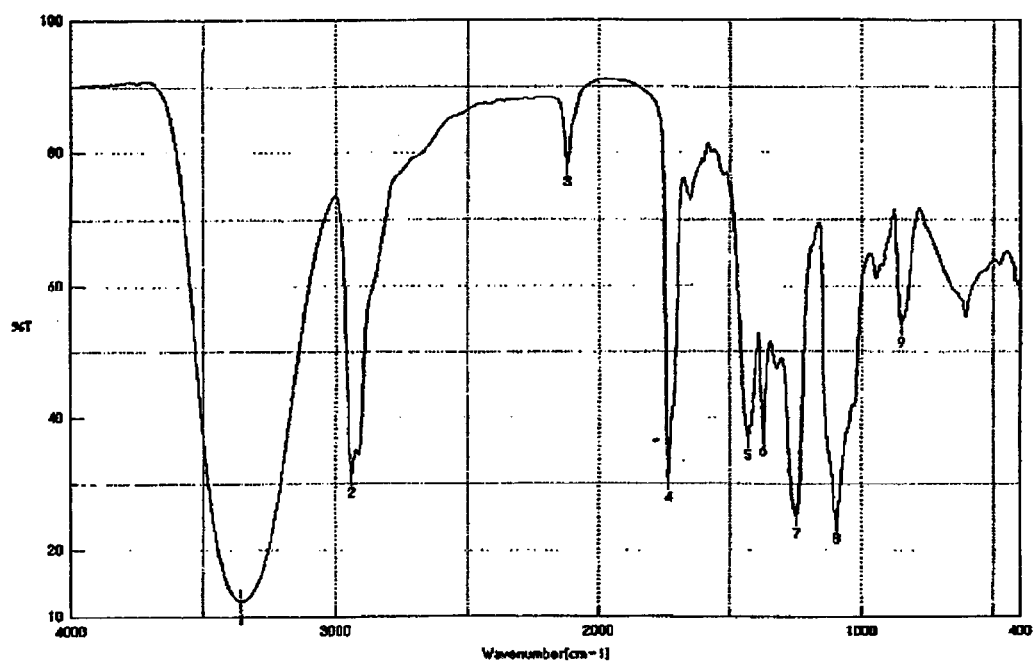
FIG. 5 An IR absorption spectrum of film of photosensitive resin J produced in Example 9.

Furthermore, the prepared photosensitive composition was applied onto a PET film and dried, to thereby form a coating film having a film thickness of 3 μm. The coating film was peeled from the PET substrate, and an IR absorption spectrum of the film (i.e., a photosensitive resin J film) was measured. The spectrum was found to have an absorption attributed to an azido group at 2,020 cm$^{-1}$. FIG. 5 illustrates the IR absorption spectrum.

Example 10

Synthesis of Photosensitive Resin K and Preparation of a Photosensitive Composition Diacetoneacrylamide-polyvinyl alcohol copolymer ("DF-20," product of Japan VAM & Poval Co., Ltd.) (40 g) was dissolved in water (400 g), and photosensitive material C (4 g) produced in Example 2 and phosphoric acid (2 g) were added to the solution. The mixture was allowed to react at 50° C. for 48 hours. Percent acetalization, determined through GPC (gel permeation chromatography), was 98%. The acetalization amount, calculated from the percent acetalization, was 0.8 mol % based on the copolymer. Thereafter, phosphoric acid was removed through treatment with an ion exchange resin, to thereby yield a photosensitive liquid containing a photosensitive resin in which photosensitive material C is bonded to diacetoneacrylamide-polyvinyl alcohol copolymer via an acetal bond in a pendant manner. The photosensitive liquid was diluted with water, to thereby prepare a photosensitive composition having a photosensitive resin concentration of 6 weight %.

The thus-prepared photosensitive composition was applied onto a glass plate and dried, to thereby form a coating film having a film thickness of 1.0 μm. A test mask (product of TOPPAN Printing Co., Ltd.) was firmly attached to the coating film, and the film was irradiated via the mask with light of an ultrahigh-pressure mercury lamp (UV illuminance: 5 mW/cm$^2$, determined by means of an illuminometer "UV-35," product of ORC Manufacturing Co., Ltd.) for 15 seconds. Subsequently, the light-exposed film was developed with water over 60 seconds and dried. Thus, a clear pattern having a line width of 30 μm and no development residue was obtained through the development step.

Example 11

Synthesis of Photosensitive Resin L

Polyvinyl alcohol-polyethylene glycol graft copolymer ("Kollicoat IR," product of BASF) (40 g) was dissolved in water (300 g), and photosensitive material C (4 g) produced in Example 2 and phosphoric acid (2 g) were added to the solution. The mixture was allowed to react at 50° C. for 48 hours. Percent acetalization, determined through GPC (gel permeation chromatography), was 98%. The acetalization amount, calculated from the percent acetalization, was 0.8 mol % based on the copolymer. Thereafter, phosphoric acid was removed through treatment with an ion exchange resin, to thereby yield a photosensitive liquid containing a photosensitive resin in which photosensitive material C is bonded to polyvinyl alcohol-polyethylene glycol graft copolymer via an acetal bond in a pendant manner. The photosensitive liquid was diluted with water, to thereby prepare a photosensitive composition having a photosensitive resin concentration of 10 weight %.

The thus-prepared photosensitive composition was applied onto a glass plate and dried, to thereby form a coating film having a film thickness of 0.6 μm. A test mask (product of TOPPAN Printing Co., Ltd.) was firmly attached to the coating film, and the film was irradiated via the mask with light of an ultrahigh-pressure mercury lamp (UV illuminance: 5 mW/cm$^2$, determined by means of an illuminometer "UV-35," product of ORC Manufacturing Co., Ltd.) for 60 seconds. Subsequently, the light-exposed film was developed with water over 40 seconds and dried. Thus, a clear pattern having a line width of 30 μm and no development residue was obtained through the development step.

Comparative Example 1

Synthesis of Comparative Photosensitive Resin M

Polyvinyl alcohol (EG-30, product of The Nippon Synthetic Chemical Industry Co., Ltd.) (40 g) was dissolved in water (400 g), and comparative photosensitive material I (4 g) produced in Comparative Synthesis Example 2 and phosphoric acid (2 g) were added to the solution. The mixture was allowed to react at 60° C. for 24 hours. Percent acetalization, determined through GPC (gel permeation chromatography), was 98%. The acetalization amount, calculated from the percent acetalization, was 0.8 mol % based on polyvinyl alcohol. Thereafter, phosphoric acid was removed through treatment with an ion exchange resin, to thereby yield a photosensitive liquid containing a photosensitive resin in which comparative photosensitive material I is bonded to polyvinyl alcohol via an acetal bond in a pendant manner. The photosensitive liquid was diluted with water, to thereby prepare a photosensitive composition having a photosensitive resin concentration of 6 weight %.

The thus-prepared photosensitive composition was applied onto a glass plate and dried, to thereby form a coating film having a film thickness of 1.0 μm. A test mask (product of TOPPAN Printing Co., Ltd.) was firmly attached to the coating film, and the film was irradiated via the mask with light of an ultrahigh-pressure mercury lamp (UV illuminance: 5 mW/cm$^2$, determined by means of an illuminometer "UV-35," product of ORC Manufacturing Co., Ltd.) for 15 seconds. Subsequently, the light-exposed film was developed with water over 60 seconds and dried. Thus, a clear pattern having a line width of 50 μm and no development residue was obtained through the development step. However, a pattern having a line width of 30 μm was partially clear but included some thick portions. The resolution of the pattern was lower than that attained in Example 1.

Test Example 1

Solubility of each of the photosensitive compounds produced in Comparative Synthesis Examples 1 to 2 and Examples 2 to 5 (comparative photosensitive materials H and I, and photosensitive materials C to F) in 100 g of neutral water (water temperature: 20° C.) was assessed. The solubility in an aqueous phosphoric acid solution (liquid temperature: 20° C.) obtained by mixing phosphoric acid (4 g) and water (100 g), was also determined. Table 1 illustrates the amount of each photosensitive compound dissolved in each medium.

TABLE 1

|  | Solubility in water (100 g) | Solubility in aq. phosphoric acid solution (104 g) |
|---|---|---|
| Comp. Photosensitive material H (Comp. Synth. Ex. 1) | ≤0.1 g | ≤0.1 g |
| Comp. Photosensitive material I (Comp. Synth. Ex. 2) | ≤0.1 g | 0.2 g (complete dissolution) 0.4 g (partial dissolution) |
| Photosensitive material C (Ex. 2) | ≤0.1 g | 5 g (complete dissolution) |
| Photosensitive material D (Ex. 3) | ≤0.1 g | 5 g (complete dissolution) |
| Photosensitive material E (Ex. 4) | ≤0.1 g | 5 g (complete dissolution) |
| Photosensitive material F (Ex. 5) | ≤0.1 g | 5 g (complete dissolution) |

As is clear from Table 1, the photosensitive compounds produced in Examples 2 to 5 falling within the scope of an aspect of the present invention (photosensitive materials C to F) exhibited very high solubility in aqueous phosphoric acid solution. In contrast, comparative photosensitive material H produced in Comparative Synthesis Example 1 exhibited very low solubility in aqueous phosphoric acid solution. Comparative photosensitive material I produced in Comparative Synthesis Example 2 was dissolved in aqueous phosphoric acid solution in a more amount as compared with comparative photosensitive material H produced in Comparative Synthesis Example 1, but the solubility thereof is lower than that of photosensitive materials C to F produced in Examples 2 to 5.

Test Example 2

Each of the 6 weight % photosensitive compositions produced in Example 9 and Comparative Example 1 was placed in a plastic container, and the container was stored in a refrigerator at 4° C. in the dark for one year. The viscosity of the composition was measured at 25° C. on day 0 (start), 6 months after the start, and 1 year after the start. Table 2 illustrates the results.

TABLE 2

|  | Day 0 | 6 Months | 1 Year |
|---|---|---|---|
| Photosensitive resin J (Ex. 9) | 260 mPa | 260 mPa | 260 mPa |
| Comparative photosensitive resin M (Comp. Ex. 1) | 300 mPa | 400 mPa | 600 mPa |

As is clear from Table 2, the photosensitive composition, containing photosensitive resin J of Example 9 exhibited no rise in viscosity even after storage in a plastic container placed in a refrigerator at 4° C. in the dark for one year, indicating excellent storage stability. In contrast, the photosensitive composition, containing comparative photosensitive resin M of Comparative Example 1 exhibited an increase in viscosity over time. One conceivable reason for attaining a constant viscosity of the photosensitive composition of an aspect of the present invention for a long period of time is that a very high solubility of the photosensitive compound of an aspect of the present invention in acidic aqueous phosphoric acid solution realizes uniform bonding of the photosensitive compound to a base polymer during acetalization of the polymer. In this case, cohesion of photosensitive groups is prevented. In contrast, the photosensitive compound of Comparative Example 1 exhibits water solubility in an acidity range lower than that of the photosensitive compound of an aspect of the present invention. Thus, the photosensitive resin can be completely dissolved at the end of the reaction, but is in a dispersion state at an initial stage of the reaction. Therefore, conceivably, a microscopic bonding feature of the photosensitive compound to the photosensitive resin in a pendant manner is not uniform, causing partial cohesion of resin molecules during a long-term storage, resulting in a rise in viscosity.

The invention claimed is:

1. A photosensitive compound, represented by the following formula (1) or formula (2)

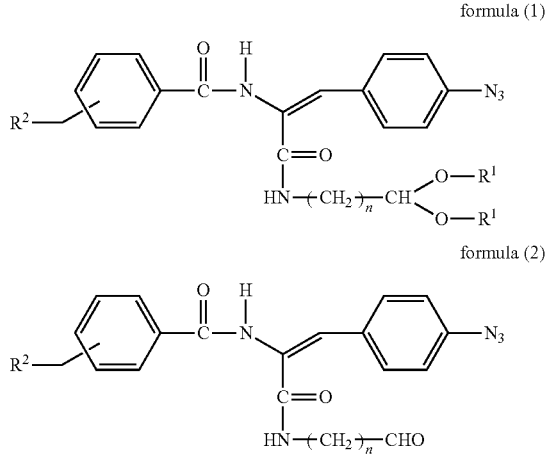

wherein:
n is an integer of 1 to 3;
$R^1$ represents a C1 to C6 linear or branched alkyl group, or a C2 to C6 alkylene group formed from two $R^1$ together; and
$R^2$ represents —$NR^3R^4$, where $R^3$ and $R^4$ each independently represent a C1 to C6 linear or branched alkyl group, or alkenyl group, or $R^3$ and $R^4$ together form a C2 to C6 linear or branched alkylene group, or form a C3 to C8 linear or branched alkylene group, or alkenylene group which may include an oxygen atom or a nitrogen atom.

2. The photosensitive compound according to claim 1, wherein:
$R^1$ is a methyl group or an ethyl group; and
$R^2$ is a group selected from the following groups,

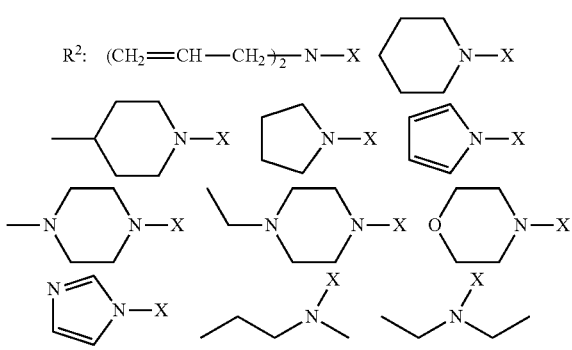

where X represents a substitution position.

3. A photosensitive resin formed by attaching the photosensitive compound according to claim 1 to a polymer having a structure in which at least two repeating units derived from vinyl alcohol are linked together, via an acetal bond in a pendant manner.

4. The photosensitive resin according to claim 3, comprising a repeating unit represented by the following formula (3):

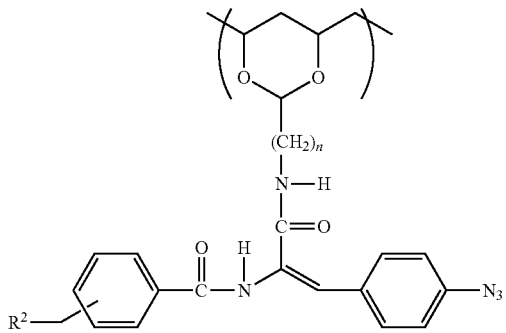

wherein n is an integer of 1 to 3, and $R^2$ represents a group selected from the following groups,

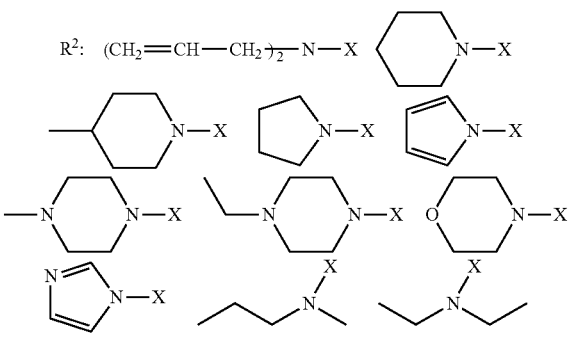

where X represents a substitution position.

5. The photosensitive resin according to claim 4, wherein the polymer is a copolymer of vinyl alcohol and at least one species selected from the group consisting of vinyl acetate, diacetoneacrylamide, acrylamide, acrylic acid, and polyethylene glycol.

6. A photosensitive composition comprising:
the photosensitive resin according to claim 4; and
water.

7. The photosensitive resin according to claim 3, wherein the polymer is a copolymer of vinyl alcohol and at least one species selected from the group consisting of vinyl acetate, diacetoneacrylamide, acrylamide, acrylic acid, and polyethylene glycol.

8. A photosensitive composition comprising:
the photosensitive resin according to claim 7.

9. A photosensitive composition comprising:
the photosensitive resin according to claim 3; and
water.

10. A compound represented by the following formula (4),

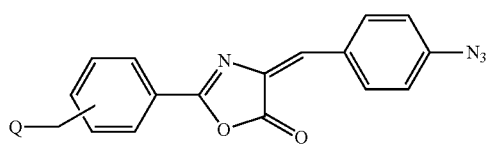

wherein Q represents a halogen atom.

11. A compound represented by the following formula (6),

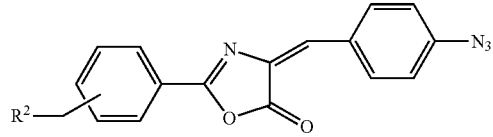

formula (6)

wherein $R^2$ represents $-NR^3R^4$, where $R^3$ and $R^4$ each independently represent a C1 to C6 linear or branched alkyl group, or alkenyl group, or $R^3$ and $R^4$ together form a C2 to C6 linear or branched alkylene group, or form a C3 to C8 linear or branched alkylene group, or alkenylene group which may include an oxygen atom or a nitrogen atom.

* * * * *